United States Patent [19]
Elder et al.

[11] Patent Number: 5,603,963
[45] Date of Patent: Feb. 18, 1997

[54] METHOD FOR THE TREATMENT OF RETROVIRAL DISEASES SUCH AS ACQUIRED IMMUNE DEFICIENCY SYNDROME UTILIZING (PSEUDO)HALOGEN COMPLEXES OF GOLD(1)

[75] Inventors: Richard C. Elder; Katherine T. Elder, both of Cincinnati, Ohio

[73] Assignee: University of Cincinnati, Cincinnati, Ohio

[21] Appl. No.: 281,951

[22] Filed: Jul. 28, 1994

[51] Int. Cl.$^6$ .......................... A61K 33/24; A61K 33/42; A61K 33/04

[52] U.S. Cl. .......................... 424/649; 424/604; 424/609; 424/702

[58] Field of Search .................... 424/649, 604, 424/609, 702

[56] References Cited

U.S. PATENT DOCUMENTS

| | | | |
|---|---|---|---|
| 3,718,679 | 2/1973 | McGusty et al. | 424/215 |
| 3,718,680 | 2/1973 | McGusty et al. | 424/198 |
| 3,784,687 | 1/1974 | McGusty et al. | 424/212 |
| 3,792,165 | 2/1974 | McGusty et al. | 424/215 |
| 3,842,107 | 10/1974 | Sutton et al. | 424/215 |
| 3,903,274 | 9/1975 | Sutton et al. | 424/223 |
| 4,405,311 | 9/1983 | Greatbatch | 604/20 |
| 4,606,354 | 8/1986 | Jacob | 128/784 |
| 5,051,425 | 9/1991 | Nakai | 514/256 |
| 5,055,457 | 10/1991 | Schrimer et al. | 514/59 |
| 5,102,908 | 4/1992 | Albeck et al. | 514/467 |
| 5,116,822 | 5/1992 | De Clerq et al. | 514/49 |
| 5,254,587 | 10/1993 | Burzynski | 514/563 |

FOREIGN PATENT DOCUMENTS

| | | |
|---|---|---|
| 8901764 | 3/1989 | WIPO . |
| 9014825 | 12/1990 | WIPO . |

OTHER PUBLICATIONS

*Aurothiolates Inhibit HIV–1 Infectivity by Gold*(1) *Ligand Exchange with a Component of the Virion Surface,* Okada et al., Virology 192, pp. 631–642 (1993).

*Dicyanogold* (1) *is a Common Human Metabolite of Different Gold Drugs,* Elder et al., The Journal of Rheumatology, 20:2, pp. 268–272 (1993).

Graham et al, "Medicinal Chemistry of Gold", Agents Actions Suppl., 44(Variability in Response to Anti-Rheumatic Drugs), 209–17 (1993).

Dubhghaill et al, "Gold Complexes in cancer chemotheraphy", Met. Complexes Cancer Chemother., 221–48; Editor: Keppler (1993).

*Primary Examiner*—S. Mark Clardy
*Assistant Examiner*—Deborah Lambkin
*Attorney, Agent, or Firm*—Frost & Jacobs

[57] ABSTRACT

A method of treating retroviral diseases such as AIDS in an infected host is provided. The method comprises administering a therapeutically effective amount of at least one (pseudo)halogen complex of gold(I) in a pharmaceutically acceptable carrier. The (pseudo)halogen complex in gold(I) can be chosen from the group consisting of:

R—Au—[CN], R—Au—[SCN], and R—Au—[SeCN].

R may be chosen from the group consisting of: phosphines (such as triethylphosphine); halogens (such as chlorine); and pseudohalogens (such as an additional cyano, thiocyanato or selenocyanato moiety). When R is an additional cyano moiety, the complex is termed a dicyanogold(I) complex, i.e., $[Au(CN)_2]^-$, and is preferably employed as an alkali, ammonium or alkaline earth salt. When R is another moiety, the complex may be either neutral or anionic in nature, and any anionic complexes are also preferably present as alkali, ammonium or alkaline earth salts. Suitable complexes include: chlorogold(I) cyanide, triethylphosphinegold(I) cyanide, and dicyanogold(I).

15 Claims, No Drawings

METHOD FOR THE TREATMENT OF RETROVIRAL DISEASES SUCH AS ACQUIRED IMMUNE DEFICIENCY SYNDROME UTILIZING (PSEUDO)HALOGEN COMPLEXES OF GOLD(I)

The present application relates to the use of gold complexes as treatments for diseases caused by retroviruses, particularly Acquired Immune Deficiency Syndrome (AIDS). These complexes include (pseudo)halogen complexes of gold(I) such as:

R—Au—[CN], R—Au—[SCN], and R—Au—[SeCN].

R may be chosen from the group consisting of: phosphines (such as triethylphosphine); halogens (such as chlorine); and pseudohalogens (such as an additional cyano, thiocyanato or selenocyanato moiety). When R is an additional cyano moiety, the complex is termed a dicyanogold(I) complex, i.e., $[Au(CN)_2]^-$, and is preferably employed as an alkali, ammonium or alkaline earth salt. When R is another moiety, the complex may be either neutral or anionic in nature, and any anionic complexes are also preferably present as alkali, ammonium or alkaline earth salts. These complexes are capable of efficiently entering the cells in which the retroviruses reside, and inhibit replication of the retrovirus (e.g., HIV).

BACKGROUND OF INVENTION

AIDS is the leading cause of death in men between the ages of 25 and 44 in 60% of cities in the United States. Initial work on the disease centered on the search for a causative agent, and a critical step in the understanding of AIDS came with the discovery of the retroviral basis of the disease by Gallo, et al. (*Science*, 220:865–868 (1983)) and Montagnier (Barre-Sinoussi, et al. *Science* 220:868–71 (1983)).

Retroviruses are simple structures which utilize RNA as their genetic material. In order to complete its life cycle, the retrovirus must first enter a cell, where the retrovirus then uses its RNA as a template for the synthesis of DNA. To accomplish this synthesis of genetic material which ultimately results in the formation of new viral cells, the virus encodes a unique protein, RNA dependent DNA polymerase (reverse transcriptase). Since this enzyme is not found in eukaryotic cells, reverse transcriptase is an obvious target for drugs which could disrupt replication of the AIDS virus without affecting cellular processes, and indeed much of the research into treatments for retroviral ailments such as AIDS has focused on the inhibition of the synthesis of DNA by reverse transcriptase.

The retrovirus which causes AIDS is human immunodeficiency virus ("HIV"). HIV is part of a group of lentiviruses, or slow viruses, which cause diseases which develop extremely slowly. In some HIV-infected patients, for example, symptoms of AIDS do not appear for 10 years or more. HIV undergoes different types of cycles in depending upon the type of cell infected. The major cells infected by HIV, however, are those of the immune system which contain the antigen CD4 on their cell surfaces. These cell types include $T_{helper}$ cells and macrophages. In the $T_{helper}$ cells, the virus undergoes a lytic cycle in which replication of the virus ultimately leads to lysis of the cells. Since $T_{helper}$ cells play a critical role in both humoral and cellular immunity, destruction of these cells compromises both aspects of the immune system. In macrophages, on the other hand, HIV generally undergoes a non-lytic behavior in which viral particles are produced, but at relatively low levels. In this type of cell, a "latent state" of viral infection is observed, and it is therefore believed that the macrophages are the main reservoir of the retrovirus in the patient.

The first agent approved by the FDA for the treatment of AIDS was azidothymidine (AZT). AZT, an analog of thymidine, is incorporated into the growing DNA strand during synthesis by the viral reverse transcriptase. Its incorporation prevents further synthesis of the DNA strand, and therefore interferes with viral replication. Other drugs such as dideoxyinosine (DDI) inhibit HIV replication in a similar fashion. While drugs such as AZT and DDI have been shown to be effective in slowing the progress of the disease, both produce significant side effects. In particular, these compounds can be incorporated into cellular DNA, leading to interference with normal cellular function. Thus, there is a need for drugs which are incapable of being incorporated into cellular DNA for use either alone or in combination with other treatments.

Gold-based drugs have been used for over 100 years for the treatment of several diseases. In the 19th century, gold cyanide was used for the treatment of tuberculosis, while more recently the primary use of gold drugs has been in the treatment of rheumatoid arthritis. The principal drugs currently used for inducing remission in rheumatoid arthritis are sodium gold(I) thiomalate (Myochrysine), gold(I) thioglucose (Solganol), and triethylphosphinegold(I)tetraacetylthioglucose (Auranofin). Although the therapeutic mechanism of these drugs has not been clearly established, numerous possibilities have been suggested. These include interference with copper metabolism, inhibition of lysosomal enzymes such as collagenase, and interference with steroid metabolism (Sadler, P., *Adv. Inorg. Chem.* 36:1–48 (1991)). Other theories involve the modification of cellular activities, including cellular transport functions, through the interaction of thiol groups on the membrane. Such modifications may also include a modulation of the lymphocyte activation observed in arthritis (Smith, W. E. and J. Reglinski, *Persp. Inorg. Chem.* 1:183–208 (1991)). Recently, gold-based drugs, particularly Auranofin, have also been used to treat asthma and psoriasis. This long history of the use of gold-based drugs has also shown that they are well-tolerated by patients, and a considerable amount of information on tolerance levels is available.

While there have been suggestions that certain gold-based drugs may be effective in treating AIDS, none have been proven to be effective. PCT/FR90/00387, for example, suggests that gold(I) thiol complexes, including gold(I)thioglucose (Solganol), inhibit HIV reverse transcriptase in in vitro assays. The relevance of this information for the treatment of HIV infection is questionable, since viral replication of HIV within an infected host takes place within the target cells. Gold thioglucose, however, is inherently unable to enter cells, and it consequently does not have access to the reverse transcriptase. The proposed route for overcoming this problem is the introduction of the gold compound through the use of liposomes to permit specific delivery to target cells. The effectiveness of such a delivery system, however, has not been demonstrated.

More recently, it has been demonstrated that gold(I) complexes such as bis(thioglucose)gold(I)inhibit the infectivity of HIV in the lymphoblastic leukemia cell line CEM in a cell culture. Although the compound does inhibit HIV reverse transcriptase in an in vitro system, the primary effect of the compound is claimed to be at the level of the gp40 antigen on the cell surface. Binding of HIV requires gp120, which is attached to the cell surface through gp40. Interference with the glycoprotein interaction prevents attachment of the virus to the potentially susceptible cell. While these experiments show a significant effect of bis(thioglucose)gold(I) on HIV infection in vitro, the cell culture system in which they were carried out permits concentrations of the compound in the 6ppm range. Such a level, however, is significantly higher than concentrations routinely found in the bloodstream of patients treated with gold-based drugs, and may very well be a toxic level for most people.

Thus, while it has been suggested that certain gold-based drugs may be effective in treating AIDS, none have been proven in in vivo studies. More importantly, some of these proposals would intuitively appear to be ineffective because of the current understanding of AIDS and gold-based drugs.

SUMMARY OF THE INVENTION

The present invention provides a method of treating retroviral diseases such as AIDS in an infected host. The method comprises administering a therapeutically effective amount of at least one (pseudo)halogen complex of gold(I) in a pharmaceutically acceptable carrier. The (pseudo)halogen complex of gold(I) may be chosen from the group consisting of R—Au—[CN], R—Au—[SCN], and R—Au—[SeCN].

R may be chosen from the group consisting of: phosphines (such as triethylphosphine, trimethylphosphine, and triphenylphosphine); halogens (such as chlorine, fluorine, bromine and iodine); and pseudohalogens (such as an additional cyano, thiocyanato or selenocyanato moiety). When R is an additional cyano moiety, the complex is termed dicyanogold(I), i.e., $[Au(CN)_2]^-$, and is preferably employed as an alkali, ammonium or alkaline earth salt. When R is another moiety, the complex may be either neutral or anionic in nature. Any anionic complexes are also preferably present as alkali, ammonium or alkaline earth salts. Other suitable complexes include triethylphosphinegold(I)cyanide, chlorogold(I) cyanide, dithiocyanatogold(I), and diselenocyanatogold(I).

DETAILED DESCRIPTION

Applicants initial inquiry was centered on the fact that only complexes which can readily enter cells would be expected to attack the replication process of the retrovirus, since this process takes place within the host's cells. Applicants have now found that (pseudo)halogen complexes of gold(I), including dicyanogold(I), are readily taken up by cells, and are effective in inhibiting the replication of the HIV virus. The term "pseudohalogen" refers to such moieties as cyano, thiocyanato, and selenocyanato, and "(pseudo)halogen complexes" refers to complexes having halogen and/or pseudohalogen moieties. Thus, these complexes are effective in treating retroviral diseases such as AIDS.

A powerful means to attack the AIDS virus (HIV) would be to find a specific inhibitor of the viral reverse transcriptase. If this enzyme cannot function, viral replication cannot take place. The significant aspect of the viral life cycle which must be considered is that the viral replication takes place intracellularly. Thus, agents which may work in a test tube to inhibit the enzyme activity will have no effect on the virus itself unless the agent is capable of entering cells and developing an effective intracellular concentration. While Solganol may inhibit the enzyme in vitro, studies from our laboratory and others indicated that patients treated for rheumatoid arthritis with the drug solganol have very low levels of gold inside cells (less than 5% of the amount found in blood). These levels are well below the levels required to inhibit the enzyme in vitro. Further, studies from our laboratories indicate that in patients injected with Solganol, the drug itself does not circulate intact. Chromatographic analysis indicates that the drug is readily converted into other gold containing species, most of which have yet to be identified.

One compound has been identified in the bloodstream of patients administered Solganol and other common antiarthritis drugs such as Myochrysine and Auranofin. Dicyanogold, $[Au(CN)_2]^-$, is found at varying levels in patients treated with these common antiarthritis gold-based drugs, particularly in smokers. This compound seems to be well tolerated by patients, with urine levels of $[Au(CN)_2]^-$ of as high as 30% of the total gold in the urine (concentrations as high as 100 ppb) observed.

Applicants' testing has shown that $[Au(CN)_2]^-$ is readily taken up by cells, the essential criterion for a therapeutic agent. Experiments were done in which whole blood or red blood cells were washed and resuspended in a balanced salt solution, and then incubated at 37° with 200 ppb $[Au(CN)_2]^-$. After 1 hour of incubation, cells were washed with balanced salt, centrifuged, then resuspended in water to lyse the cells. The resulting suspension was centrifuged at 20,000 rpm to separate the membrane and lysate (soluble protein) fractions. Both membrane and lysate fractions were analyzed for total gold by flow injection analysis using an inductively coupled plasma-mass spectrometer (ICP-MS). Similar tests were performed with Myochrysine, and the results are shown below:

| Fraction | Dicyanogold | | Myochrysine | |
| --- | --- | --- | --- | --- |
| | Whole Blood | RBC | Whole Blood | RBC |
| Supernatant | 31% | 5% | 90% | 84% |
| Cell lysate | 65% | 90% | 4% | 6% |
| Membranes | 4% | 5% | 6% | 10% |

When whole blood was used in the incubation, 65% of the total gold was found in the cell lysate after the 1 hour incubation. With red blood cell incubation, over 90% of the gold was found in the lysate. In both cases, however, only about 5% of the total gold was found in the membrane fraction. In contrast, the Myochrysine tests indicated that only about 5% of the total gold was found in the cell lysate, with close to 90% of the gold remaining in the incubation medium. These results clearly demonstrate that $[Au(CN)_2]^-$ enters red blood cells quite readily.

In another set of experiments, a lymphocyte cell line was incubated with $[Au(CN)_2]^-$ in order to determine the effect of the compound on the rate of growth of these cells as well as the degree to which the gold was able to enter the cells. The cells used for these experiments were H9 lymphocytes, developed in Robert Gallo's laboratory at the National Institutes of Health, Bethesda, Md. These cells were used because they are capable of supporting infection by HIV in a cell culture system. Thus, H9 cells are an appropriate model for the study of the uptake of drugs which affect intracellular replication of HIV. H9 cells obtained from the American Type Culture Collection, Rockville, Md., were exposed to varying levels of $[Au(CN)_2]^-$ from 10 ppb to 100 ppb. At levels of 10 and 20 ppb, there was no significant effect on the rate of cell growth. At higher levels of gold, there was an initial significant decrease in cell number, but after several days of exposure to the compound, the cells recovered and were able to achieve normal rates of growth in as much as 100 ppb $[Au(CN)_2]^-$. Measurements of the intracellular levels of gold after incubation with $[Au(CN)_2]^-$ indicated that the H9 cells incubated had at least 25 times more gold within them than the external medium. These results are consistent with Applicants' testing on red blood cells, and demonstrate that a lymphocyte line capable of supporting the replication of the AIDS virus not only absorbs gold, but is also capable of accumulating gold when it is introduced in the form of $[Au(CN)_2]^-$.

Gold(I) complexes are generally rapid to react (Puddephatt, R. J. in *The Chemistry of Gold*, Elsevier, N.Y., 1978, p 193) and thus easily bind to target sites. Thus, once it has entered HIV-infected cells (as demonstrated above), a (pseudo)halogen complex of gold(I) such as dicyanogold(I) will inhibit the retroviral reverse transcriptase, thereby providing an effective treatment for AIDS. Similarly, other (pseudo)halogen complexes of gold(I) will also be effective in treating retroviral diseases such as AIDS.

Accordingly, Applicants have discovered an effective treatment for AIDS, comprising the step of administering a therapeutically effective amount of at least one (pseudo)cyanogold(I) complex of gold(I) in a pharmaceutically acceptable carrier. By "(pseudo)halogen complex of gold(I)", Applicants intend to include, among others, dicyanogold(I), dithiocyanatogold(I), and diselenocyanatogold(I). These complexes readily enter host cells where they inhibit the replicative process of HIV, thereby providing an effective treatment for AIDS. These same complexes will also be effective in treating other retroviral diseases in the same fashion.

The (pseudo)halogen complexes of gold(I) which may be employed in the method of the present invention include: R—Au—[CN], R—Au—[SCN], and R—Au—[SeCN]. R may be chosen from the group consisting of: phosphines, halogens, and pseudohalogens. Suitable phosphines include triethylphosphine, trimethylphosphine, and triphenylphosphine. Suitable halogens include chlorine, bromine, fluorine, and iodine. Acceptable pseudohalogens include an additional cyano, thiocyanato, or selenocyanato moiety. When a halogen or pseudohalogen is employed as R, the complex is preferably present as an alkali, ammonium or alkaline earth metal salt due to the anionic nature of the complex. Thus, the following is a list of suitable complexes which may be employed in the present invention:

chlorogold(I) cyanide: $[Cl—Au—CN]^-$
triethylphosphinegold(I) cyanide: $[C_2H_5]_3P—Au—CN$
dicyanogold(I): $[Au—[CN]_2]^-$
dithiocyanatogold(I): $[Au—[SCN]_2]^-$
diselenocyanatogold(I): $[Au—[SeCN]_2]^-$ Having shown and described the preferred embodiments of the present invention, further adaptations of the method described herein can be accomplished by appropriate modifications by one of ordinary skill in the art without departing from the scope of the present invention. Several of such potential modifications have been mentioned, and others will be apparent to those skilled in the art. Accordingly, the scope of the present invention should be considered in terms of the following claims and is understood not to be limited to the details of the process shown and described in the specification.

What we claim is:

1. A method of treating HIV intracellularly in an infected host comprising the step of administering a therapeutically effective amount of at least one (pseudo)halogen complex of gold(I) in a pharmaceutically acceptable carrier, wherein said (pseudo)halogen complex of gold(I) is chosen from the group consisting of:

R—Au—CN, R—Au—[SCN], and R—Au—[SeCN]

wherein R is chosen from the group consisting of: phosphines, halogens, and (pseudo)halogens.

2. A method of claim 1, wherein said HIV causes AIDS.

3. The method of claim 1, wherein R is chosen from the group consisting of: triethylphosphine, trimethylphosphine, triphenylphosphine, $F^-$, $Cl^-$, $Br^-$, $I^-$, $[CN]^-$, $[SCN]^-$, and $[SeCN]^-$.

4. The method of claim 3, wherein R is $[CN]^-$.

5. The method of claim 3, wherein said complex is triethylphosphinegold(I) cyanide.

6. The method of claim 3, wherein said complex is chlorogold(I) cyanide.

7. The method of claim 3, wherein said complex is present as an alkali, ammonium or alkaline earth metal salt.

8. The method of claim 3 wherein said complex is chosen from the groups consisting of: dicyanogold(I), dithiocyanatogold(I), and diselenocyanatogold(I).

9. A method of treating HIV intracellularly comprising the step of administering an effective amount of at least one (pseudo)halogen complex of gold(I) in a pharmaceutically acceptable carrier, wherein said (pseudo)halogen complex of gold(I) is chosen from the group consisting of:

R—Au—CN, R—Au—[SCN], and R—Au—[SeCN], wherein R is chosen from the group consisting of: phosphines, halogens, and (pseudo)halogens.

10. The method of claim 9, wherein R is chosen from the group consisting of: triethylphosphine, trimethylphosphine, triphenylphosphine, $F^-$, $Cl^-$, $Br^-$, $I^-$, $[CN]^-$, $[SCN]^-$, and $[SeCN]^-$.

11. The method of claim 10, wherein R is $[CN]^-$.

12. The method of claim 10, wherein said complex is triethylphosphinegold(I) cyanide.

13. The method of claim 10, wherein said complex is chlorogold(I) cyanide.

14. The method of claim 10, wherein said complex is present as an alkali, ammonium or alkaline earth metal salt.

15. The method of claim 10, wherein said complex is chosen from the groups consisting of: dicyanogold(I), dithiocyanatogold(I), and diselenocyanatogold(I).

\* \* \* \* \*